US008245906B2

(12) United States Patent (10) Patent No.: US 8,245,906 B2
Crosby et al. (45) Date of Patent: Aug. 21, 2012

(54) COUNTER FOR USE WITH A MEDICAMENT DISPENSER

(75) Inventors: Gary Thomas Crosby, Ware (GB); David Vincent Elliman, Sudbury (GB); Andrew Michael Kelly, Ware (GB)

(73) Assignee: Glaxo Group Limited, Greenford, Middlesex (GB)

( * ) Notice: Subject to any disclaimer, the term of this patent is extended or adjusted under 35 U.S.C. 154(b) by 770 days.

(21) Appl. No.: 12/282,652

(22) PCT Filed: Mar. 13, 2007

(86) PCT No.: PCT/GB2007/000867
§ 371 (c)(1),
(2), (4) Date: Sep. 12, 2008

(87) PCT Pub. No.: WO2007/104964
PCT Pub. Date: Sep. 20, 2007

(65) Prior Publication Data
US 2009/0090787 A1 Apr. 9, 2009

(30) Foreign Application Priority Data
Mar. 14, 2006 (GB) .................................. 0605150.2

(51) Int. Cl.
*G06M 1/04* (2006.01)
(52) U.S. Cl. .................... 235/91 R; 235/87 R; 235/50 R
(58) Field of Classification Search ................ 235/87 R, 235/77, 87 A, 50 R, 50 A, 50 B, 91 R; 128/200.12, 128/200.14, 200.18, 200.23, 200.24, 200.22, 128/205.23, 203.15
See application file for complete search history.

(56) References Cited

U.S. PATENT DOCUMENTS

| 2,550,103 | A | 4/1951 | White |
| 3,718,114 | A | 2/1973 | Gneupel |
| 4,668,218 | A | 5/1987 | Virtanen |
| 4,817,822 | A | 4/1989 | Rand et al. |
| 4,940,966 | A | 7/1990 | Pettigrew et al. |
| 5,482,030 | A | 1/1996 | Klein |
| 5,590,645 | A | 1/1997 | Davies et al. |
| 5,657,748 | A | 8/1997 | Braithwaite |
| 5,687,710 | A | 11/1997 | Ambrosio et al. |
| 5,740,792 | A | 4/1998 | Ashley et al. |
| 5,860,419 | A | 1/1999 | Davies et al. |
| 5,873,360 | A | 2/1999 | Davies et al. |

(Continued)

FOREIGN PATENT DOCUMENTS
BE 500836 A 4/1952
(Continued)

*Primary Examiner* — Karl D Frech
(74) *Attorney, Agent, or Firm* — James P. Riek

(57) ABSTRACT

A dose counter for use with a medicament dispenser which comprises a ratchet; a first count wheel arranged to rotate about a first axis of rotation, the first count wheel including one or more ratchet drive receipt elements arranged thereon for receipt of drive from the ratchet to rotate the first count wheel about the first axis of rotation; a second count wheel arranged to rotate about the first axis of rotation, the second count wheel including a set of teeth arranged annularly thereon; and a kick wheel arranged to rotate about a second axis of rotation offset from the first axis of rotation, the kick wheel including a set of kick teeth arranged annularly thereon and in meshed relationship with the teeth of the second count wheel such that rotary motion of the kick wheel results in rotary motion of the second count wheel is described.

56 Claims, 15 Drawing Sheets

U.S. PATENT DOCUMENTS

| | | |
|---|---|---|
| 5,988,496 A | 11/1999 | Bruna |
| 6,041,779 A | 3/2000 | Juusela |
| 6,067,927 A | 5/2000 | Johnson et al. |
| 6,076,521 A | 6/2000 | Lindahl et al. |
| 6,082,358 A | 7/2000 | Scarrott et al. |
| 6,142,339 A | 11/2000 | Blacker et al. |
| 6,161,724 A | 12/2000 | Blacker et al. |
| 6,164,494 A | 12/2000 | Marelli |
| 6,182,655 B1 | 2/2001 | Keller et al. |
| 6,234,168 B1 | 5/2001 | Bruna |
| 6,240,918 B1 | 6/2001 | Ambrosio et al. |
| 6,283,365 B1 | 9/2001 | Bason |
| 6,328,037 B1 | 12/2001 | Scarrott et al. |
| 6,336,453 B1 | 1/2002 | Scarrott et al. |
| 6,360,739 B1 | 3/2002 | Rand et al. |
| 6,431,168 B1 | 8/2002 | Rand et al. |
| 6,435,372 B1 | 8/2002 | Blacker et al. |
| 6,446,627 B1 | 9/2002 | Bowman et al. |
| 6,474,331 B1 | 11/2002 | Rand et al. |
| 6,484,717 B1 | 11/2002 | Dagsland et al. |
| 6,561,384 B2 | 5/2003 | Blacker et al. |
| 6,583,040 B1 | 6/2003 | Lin |
| 6,601,582 B2 | 8/2003 | Rand et al. |
| 6,659,307 B1 | 12/2003 | Stradella |
| 6,752,153 B1 | 6/2004 | Eckert |
| 6,769,601 B2 * | 8/2004 | Haikarainen et al. ....... 235/87 R |
| 7,004,164 B2 | 2/2006 | Scarrott |
| 7,107,986 B2 | 9/2006 | Rand et al. |
| 8,113,199 B2 | 2/2012 | Augustyn et al. |
| 2002/0047021 A1 | 4/2002 | Blacker et al. |
| 2004/0255935 A1 | 12/2004 | Bruna |
| 2005/0087191 A1 | 4/2005 | Morton et al. |

FOREIGN PATENT DOCUMENTS

| | | |
|---|---|---|
| EP | 1104318 B1 | 6/2001 |
| EP | 1449557 A2 | 8/2004 |
| FR | 2022212 | 7/1970 |
| GB | 1317315 | 5/1973 |
| GB | 2364649 A | 2/2002 |
| GB | 2365778 A | 2/2002 |
| GB | 2366208 A | 3/2002 |
| GB | 2372541 A | 8/2002 |
| GB | 2372542 A | 8/2002 |
| GB | 2372543 A | 8/2002 |
| GB | 2385640 A | 8/2003 |
| WO | 9514867 A1 | 6/1995 |
| WO | 9534874 A1 | 12/1995 |
| WO | 9841258 A1 | 9/1998 |
| WO | 9856444 A1 | 12/1998 |
| WO | 9856445 A1 | 12/1998 |
| WO | 9856446 A1 | 12/1998 |
| WO | 0131578 A1 | 5/2001 |
| WO | 0137909 A1 | 5/2001 |
| WO | 02053295 A1 | 7/2002 |
| WO | 02089882 A1 | 11/2002 |
| WO | 02091293 A1 | 11/2002 |
| WO | 03028792 A1 | 4/2003 |
| WO | 03080162 A1 | 10/2003 |
| WO | 03101514 A1 | 12/2003 |
| WO | 2004001664 A1 | 12/2003 |
| WO | 2004012801 A1 | 2/2004 |
| WO | 2004026380 A2 | 4/2004 |
| WO | 2004089451 A1 | 10/2004 |
| WO | 2005002654 A2 | 1/2005 |
| WO | 2005007226 A1 | 1/2005 |
| WO | 2005017463 A2 | 2/2005 |
| WO | 2005017824 A1 | 2/2005 |
| WO | 2005041850 A1 | 5/2005 |
| WO | 2005060917 A1 | 7/2005 |
| WO | 2005079727 A2 | 9/2005 |
| WO | 2005113044 A1 | 12/2005 |
| WO | 2006032971 A2 | 3/2006 |

* cited by examiner

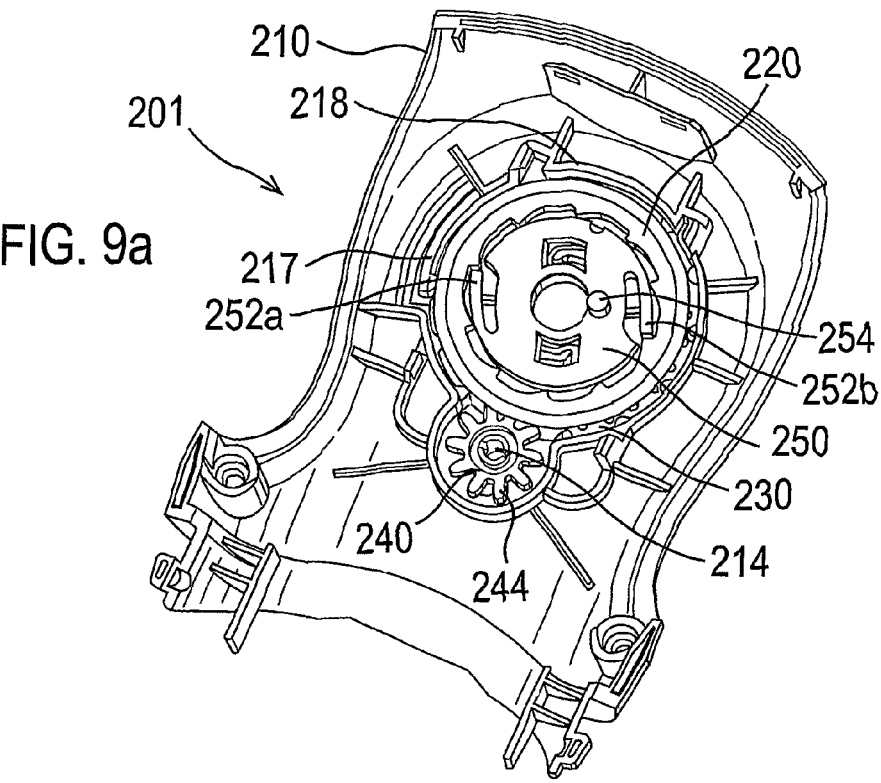
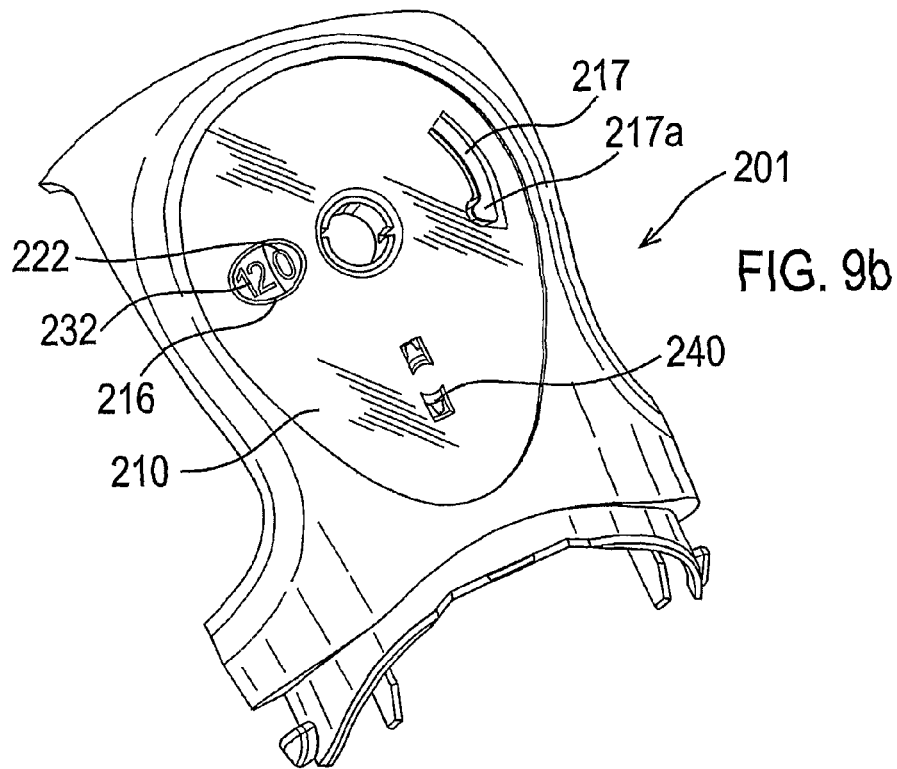

COUNTER FOR USE WITH A MEDICAMENT DISPENSER

RELATED APPLICATIONS

This application is filed pursuant to 35 U.S.C. §371 as a United States National Phase Application of International Patent Application Serial No. PCT/GB2007/000867 filed 13 Mar. 2007, which claims priority from UK patent application No. 0 605 150.2 filed on 14 Mar. 2006. The present application is further related to commonly owned U.S. Provisional Application Nos. 60/823,139, 60/823,141, 60/823,134, 60/823,143, 60/823,146, 60/823,151 and 60/823,154, all filed on 22 Aug. 2006, and U.S. Provisional Application No. 60/894,537 filed 13 Mar. 2007. The entire content of each afore-mentioned application is hereby incorporated herein by reference.

TECHNICAL FIELD

The present invention relates to a counter for use in a medicament dispenser for dispensing individual doses of medicament.

BACKGROUND OF THE INVENTION

The use of inhalation devices in the administration of medicaments, for example in bronchodilation therapy is well known. Such devices generally comprise a body or housing within which a medicament carrier is located. Known inhalation devices include those in which the medicament is delivered in aerosol form, including the well known metered dose inhaler (MDI) delivery devices. Other known inhalation devices include those in which the medicament carrier is a blister strip containing a number of discrete doses of powdered medicament. Such devices usually contain a mechanism of accessing these discrete doses, usually comprising either piercing means or means to peel a lid sheet away from a base sheet. The powdered medicament can then be accessed and inhaled. Liquid-based inhaler devices are also known.

It is advantageous to provide the patient with a dose counter for counting the number of doses of medicament dispensed or still remaining. For flexibility, the dose counter should also be suitable for use with various types of medicament dispenser including those suitable for dispensing medicament in aerosol or powder form. It is also desirable that any counter be configured to register a count only when medicament is provided to the patient for inhalation, and in particular that opportunities for false counts and/or tampering are minimised. It is further desirable that the count be clearly visible by the patient.

The Applicants have now devised a dose counter that meets some or all of the above criteria. In embodiments, the dose counter may be provided to the medicament dispenser as a separable unit, which enables ready re-use and recycling thereof. The latter benefit is particularly important where the counter comprises components, which are readily re-usable and potentially expensive to re-manufacture.

The dose counter now provided has the advantage that it may be expressed in relatively compact forms and in particular, may be accommodated in a housing that is relatively thin (i.e. one that extends upwards in the direction of the axis defined by the counter wheels to only a minor extent). The counter herein may also be arranged to count over a relatively large count range (e.g. at least 120 counts).

U.S. Pat. No. 5,988,496 describes a dose counter comprising a first count wheel and second count wheel arranged to rotate about a common axis of rotation. The first count wheel includes a drive tongue that is movable between a rest position, in which it does not co-operate with the second count wheel and a drive position, in which it co-operates with the second count wheel to cause it to rotate about the common axis of rotation. The drive tongue is forced into position by action of a cam.

Applicant's co-pending PCT Application No. WO2005/079727 describes a dose counter for use with a medicament dispenser. The dose counter comprises a first count wheel arranged to rotate about a first axis of rotation, the first count wheel including a set of primary drive teeth arranged annularly thereon for drivable rotation of the first count wheel about the first axis of rotation; and a second count wheel arranged to rotate about the same first axis of rotation. A kick wheel is arranged to rotate about a second axis of rotation offset from the first axis of rotation and provides for intermittent motion of the second count wheel.

SUMMARY OF THE INVENTION

According to one aspect of the invention there is provided a dose counter for use with a medicament dispenser, said dose counter comprising a ratchet;

a first count wheel arranged to rotate about a first axis of rotation, said first count wheel including one or more ratchet drive receipt elements arranged thereon for receipt of drive from said ratchet to rotate the first count wheel about said first axis of rotation;

a second count wheel arranged to rotate about the first axis of rotation, said second count wheel including a set of teeth arranged annularly thereon; and a kick wheel arranged to rotate about a second axis of rotation offset from the first axis of rotation, said kick wheel including a set of kick teeth arranged annularly thereon and in meshed relationship with the set of teeth of the second count wheel such that rotary motion of the kick wheel results in rotary motion of the second count wheel, wherein said first count wheel further includes at least one fixed index tooth arranged for intermittent meshing with the kick teeth of the kick wheel such that rotary motion of the kick wheel results from rotary motion of the first count wheel only when said intermittent meshing occurs.

By 'arranged annularly' herein it means arranged about a common radius (i.e. defining an annular arrangement).

Suitably, the dose counter includes a housing, which houses some or all of the other elements of the dose counter. In aspects, the housing includes a bezel and/or lens cover for the count wheels and through which indicia are generally visible.

The dose counter herein comprises a ratchet. The ratchet may be a ratchet wheel which is suitably arranged for rotation about an axis, which is preferably common with the first axis of rotation about which the first count wheel rotates. The ratchet is suitably provided with one or more ratchet drive elements such as one or more ratchet drive tongues.

Suitably, the ratchet is itself provided with one or more drive receipt elements for receipt of drive that results in movement (e.g. rotation) of the ratchet. Such drive receipt elements can take any form including one or more teeth, protrusions, and/or indents. Drive of the ratchet may be provided by a driver provided to the medicament dispenser and movable in response to user action (e.g. manual), which action typically relates to the dispensing action thereof. Suitably, the driver is adapted in use to couple with an operating mechanism of a medicament dispenser whereby actuation of the operating mechanism is transmitted to the dose counter.

The dose counter also includes a first count wheel arranged to rotate about a first axis of rotation. The first count wheel may for example, take the form of a disc or a ring.

The first count wheel includes one or more ratchet drive receipt elements arranged (e.g. in spaced fashion) thereon for receipt of drive from said ratchet to rotate the first count wheel about said first axis of rotation. The ratchet drive receipt elements can take any suitable form, including one or more teeth and/or indents.

Suitably, the ratchet drive receipt elements are arranged annularly, such as about an inner or outer circumferential wall of the first count wheel.

In a preferred aspect, the first count wheel is provided with a circular cavity (e.g. hollowed out portion) sized and shaped for receipt of the ratchet. The ratchet drive receipt elements are arranged about the inner circumferential wall (i.e. about the periphery) of the cavity for suitable ratchet drive interaction with the ratchet.

Alternatively, the first count wheel takes the form of a ring that is sized and shaped for disposed receipt of the ratchet. The ratchet drive receipt elements are arranged circumferentially about (i.e. about the periphery of) the inner wall of the ring for suitable ratchet drive interaction with the ratchet.

The dose counter further includes a second count wheel arranged to rotate about the first axis of rotation. That is to say, both the first and second count wheels rotate about the same (i.e. common) first axis of rotation.

In aspects, the first and second wheels may be arranged to rotate in the same direction or in opposing directions (i.e. one clockwise and one anti-clockwise).

The second count wheel includes a set of teeth arranged annularly (e.g. circumferentially) thereon. The teeth are therefore arranged in annular fashion at or about the circumference of the second count wheel.

In aspects, the second count wheel is arranged concentric to the first count wheel. In one aspect, the second count wheel takes the form of a ring and the first count wheel (e.g. disc or ring shape) is sized and shaped for receipt within the ring. The diameter of the first count wheel is therefore typically slightly less than that of the inner diameter (i.e. the ring hole diameter) defined by the ring-shaped second count wheel.

In one aspect, the first and second count wheels are arranged concentrically and at the same level (i.e. they share the same plane of rotation).

In another aspect, the first and second count wheels are arranged concentrically and at different levels (i.e. with different planes of rotation).

Suitably, the plane of rotation of the second counter wheel is slightly raised relative to that of the first counter wheel. In one aspect, the second count wheel is provided with a protrusion that in use, extends over and above part of the first count wheel and that may therefore function to shutter off part of the first count wheel.

The dose counter further includes a kick wheel arranged to rotate about a second axis of rotation offset from the first axis of rotation.

In one aspect, the teeth on the second count wheel are on an outer facing circumference of the second count wheel and the second axis of rotation is disposed outside the path of rotation defined by the teeth of the second count wheel.

The kick wheel includes a set of kick teeth arranged annularly, preferably circumferentially, thereon. The kick teeth are therefore arranged in annular fashion at or about the circumference of the kick wheel.

The kick teeth are in meshed relationship with the set of teeth of the second count wheel such that rotary motion of the kick wheel results in rotary motion of the second count wheel. That is to say, as the kick wheel is rotated the meshing of the kick teeth thereof with the teeth of the second count wheel results in rotation of the second count wheel.

The first count wheel further includes at least one fixed index tooth arranged for intermittent meshing with the kick teeth of the kick wheel. That is to say, the index tooth is fixed to the first count wheel and may be brought into meshed relationship with the kick teeth of the kick wheel on an intermittent basis.

Rotary motion of the kick wheel results from rotary motion of the first count wheel only when said intermittent meshing of the index tooth with the kick teeth occurs. When meshing occurs, a contact ratio of 1 between the at least one index tooth and the kick teeth is preferred, although other whole integer (2, 3 . . . ) contact ratios may be used.

Typically, the index tooth is fixed at a point at or about the circumference of the first count wheel. Rotation of the first count wheel is then arranged to bring the index tooth into meshed relationship with the kick teeth of the kick wheel at a particular point of the rotary cycle of the first count wheel. It may be therefore be appreciated that in this case, meshing occurs once during each complete rotation of the first count wheel.

In aspects, either one or both counter wheels interact with a reverse rotation (e.g. ratchet) mechanism to prevent reverse movement of the counter wheels.

Suitably, some or all teeth of some or all of the toothed parts herein have flanged form to enable effective meshing together thereof.

The dose counter herein is in one aspect, suitable for use with a medicament dispenser of any suitable type and may be provided as an insert thereto.

Suitably, the counter has a housing.

Suitably, the housing acts to house some or all of the other elements of the dose counter. The housing suitably includes a viewing window through which the count may be viewed.

Suitably, the housing is shaped to define the first axis of rotation and the second axis of rotation. Suitably, the first count wheel and/or the second count wheel mounts to the housing for rotation about the first axis of rotation and the kick wheel mounts to the housing for rotation about the second axis of rotation.

In aspects, the housing takes the form of a bezel and is suitably provided with a lens cover through which indicia of the count wheels are generally visible.

In one aspect, a shutter is provided to close off a viewing window of the dose counter at a predetermined point, particularly at the 'end of life' of the medicament product, which typically corresponds to the point at which all doses in the normal delivery cycle have been provided. In aspects, the shutter may be provided as a separate element of the dose counter or be formed as an integral part of the second counter wheel.

In one aspect, the dose counter is supplied as an assembly for insertion into the medicament dispenser.

Other aspects and features of the invention are contained in the appended claims as well as in the description of exemplary embodiments of the invention made with reference to the accompanying drawings.

BRIEF DESCRIPTION OF THE DRAWINGS

The invention will now be described with reference to the accompanying drawings in which:

FIGS. 9a and 9b respectively show underside and top views of the second dose counter;

DETAILED DESCRIPTION OF THE DRAWINGS

Figure 1:
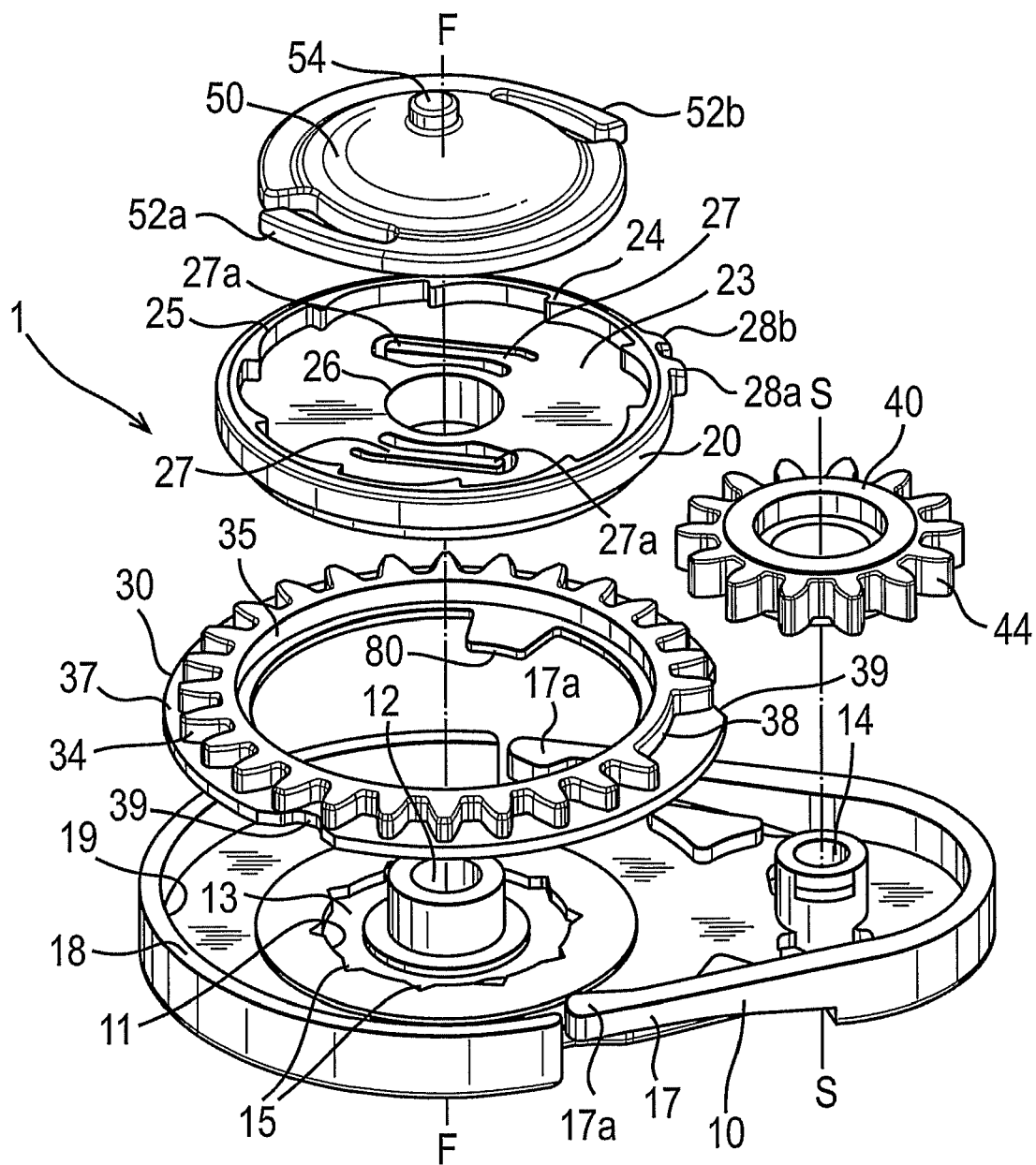
FIG. 1 shows an exploded view of a dose counter in accord with the present invention.

Referring now to FIG. 1 to 7, these show a dose counter 1 in accordance with the present invention.

The dose counter 1 comprises a housing 10 provided with first 12 and second 14 spindle mountings, each capable of defining an axis of rotation and a circumferential wall 18 defining a bezel form retainer 19. A viewing window 16 is provided to the housing to enable the viewing of the count.

First, disc-shaped count wheel 20 has 'units' (i.e. numerals) count indicia 22 provided at spaced intervals on a top face thereof. The first count wheel is provided with a central aperture 26 and a circular cavity 23 that is arranged for disposed receipt of ratchet wheel 50. Ratchet drive receipt teeth 24 are arranged about the inner circumferential wall 25 of the cavity for ratcheted drive interaction with the ratchet wheel 50. The ratchet wheel 50 itself, is sized and shaped for receipt by the circular cavity 23 of the first count wheel and is provided with two oppositely-located drive tongues 52a, 52b for ratcheted drive interaction with the ratchet drive receipt teeth 24. The ratchet wheel 50 is also provided with a drive-receiving protrusion 54 arranged in use, for drivable rotation of the ratchet wheel 50.

Second, ring form count wheel 30 also has 'tens of units' (i.e. decimals) count indicia 32 provided at spaced intervals on a top face 37 thereof and a set of teeth 34 provided in annular arrangement to the underside thereof. It may be noted that at stop position 38 a couple of the teeth 34 have been removed and further that the outer circumferential edge of top face 37 is formed with a pair of notches or indentations 39. The reasons for these features will become clear from the later description. The second count wheel 30 is also provided with a protruding shutter 80, the function of which will also be described later.

A kick wheel 40 has kick teeth 44 provided in annular arrangement around the circumference thereof.

Figure 2A:
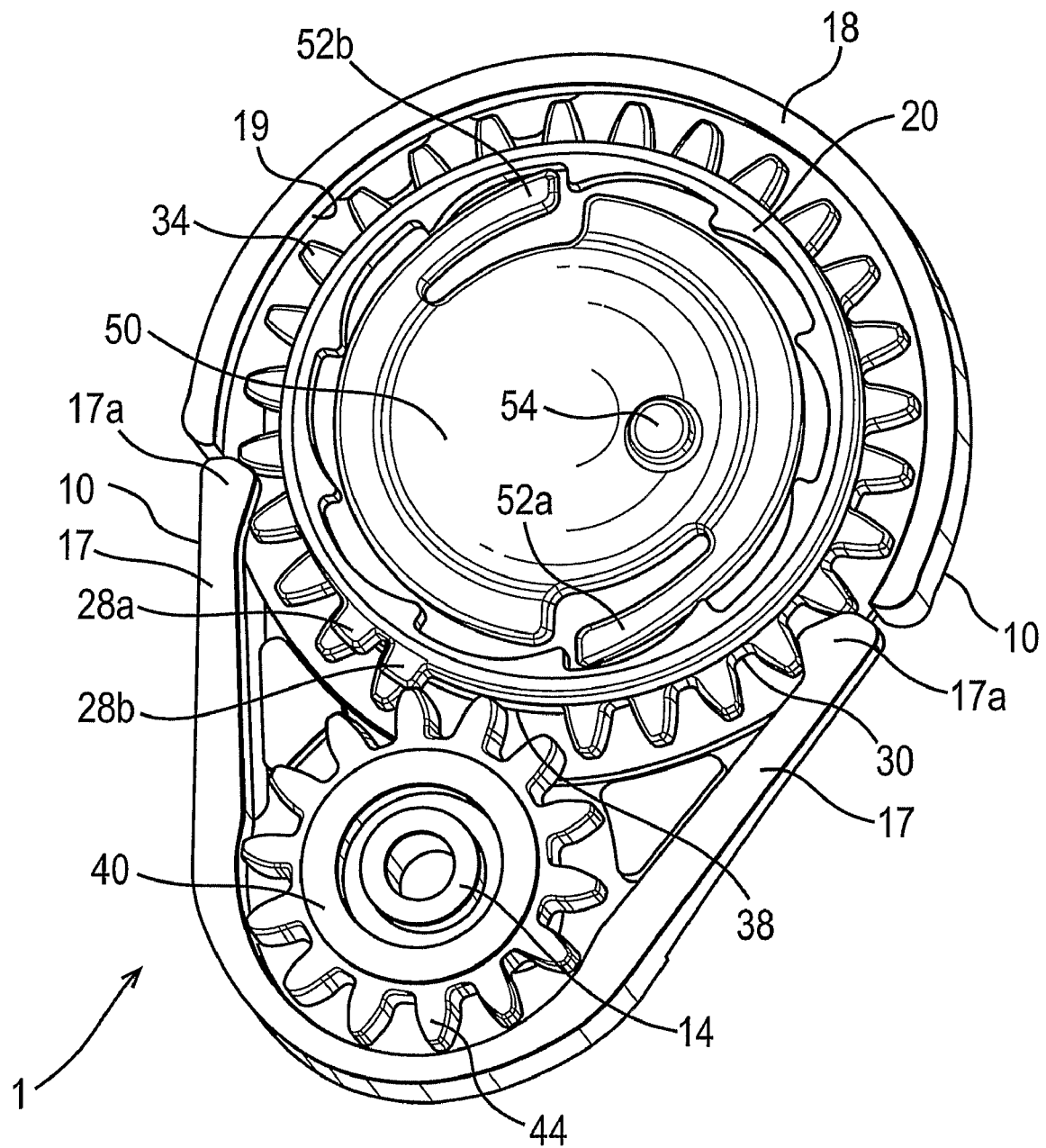
FIGS. 2a and 2b respectively show underside and top views of the dose counter of FIG. 1.
Figure 2B:
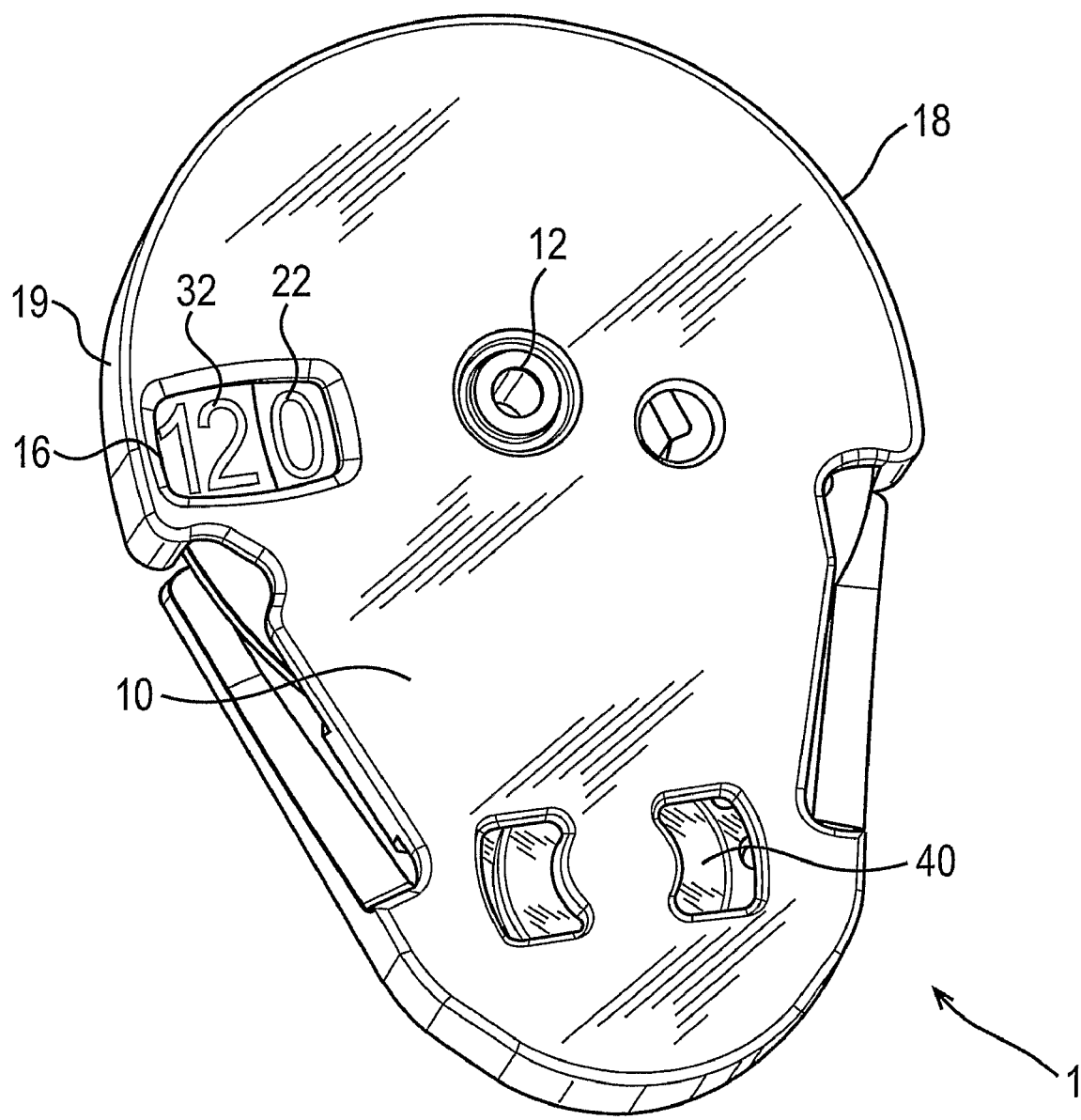

As may be best seen at FIG. 2a, when assembled, second count wheel 30 is received for rotation within the bezel form retainer 19 of the housing; and first count wheel 20 is received within the inner ring void 35 defined by ring-shaped second count wheel 30 and its central aperture 26 by first spindle 12 such that clearance exists between the first 20 and second 30 count wheels. Thus, the first 20 and second 30 count wheels are in concentric relationship, but the level of the second count wheel 30 is slightly raised relative to that of the first count wheel 20 to enable shutter 80 to protrude over and above the first count wheel 20. Ratchet wheel 50 is received within the circular cavity 23 of the first count wheel 20 such that drive tongues 52a, 52b engage with the ratchet drive receipt teeth 24. Both wheels 20, 30 and the ratchet wheel 50 are rotatable about a common, first axis of rotation F-F defined in combination by the axis of first spindle 12 and the circular shape of the bezel retainer 19. The drive-receiving protrusion 54 is offset from the first axis F-F.

Kick wheel 40 is received by second spindle 14 for rotation about a second axis of rotation S-S defined by the second spindle 14 and therefore offset from the first axis of rotation F-F. It will be appreciated that the second axis of rotation S-S is spaced from the first axis of rotation F-F to be outside the path of rotation defined by the outwardly-facing teeth 34 of the second count wheel 30. Moreover, the first and second axes F-F, S-S are parallel, or substantially parallel, to each other.

The set of kick teeth 44 of the kick wheel 40 are in meshed relationship with the set of teeth 34 of the second count wheel 30 such that rotary motion of the kick wheel 40 results in rotary motion of the second count wheel 30. In turn, ratchet drive tongues 52a, 52b of ratchet wheel 50 mesh with the ratchet drive receipt teeth 24 of the first count wheel 20 for drivable rotation of the first count wheel 20.

When the dose counter 1 is disposed in a medicament dispenser (not shown), the ratchet wheel 50 is in turn rotatable about the first axis F-F by a driver provided to the medicament dispenser driving the ratchet protrusion 54 in response to user action of the medicament dispenser.

First count wheel 20 may also be seen to be provided at its periphery with a pair of fixed index teeth 28a, 28b arranged for intermittent meshing with the kick teeth 44 of the kick wheel 40 such that rotary motion of the kick wheel 40 results from rotary motion of the first count wheel 20 only when said intermittent meshing occurs.

In a subtle aspect, it may be seen that the profile of all teeth 34, 44 has a flanged form, which is selected to optimise the various toothed engagements necessary for effective gearing and inter-operability of the parts of the counter.

In a further subtle aspect, the counter 1 is arranged to count down from '120' to a 'shuttered position'. The second count wheel 30 is thus, arranged to define fourteen equal pitches allied to twenty-six (calculated as (2×14)−2) secondary drive teeth 34 plus two missing teeth at stop position 38. The number of pitches is defined as x+2, wherein x is the highest numeral on the second count (i.e. decimals) wheel, which in turn corresponds to a highest count of 10 times x (i.e. 10×12=120, in this embodiment). The '+2' part of the sum determining the number of pitches relates to one coloured portion 82 and one shutter portion 80, as are described in more detail later.

Overall, it may be noted that the dose counter 1 has a relatively compact form and in particular, that the housing 10 is relatively thin and extends upwards in the direction of the axes F-F, S-S to only a minor extent.

Figure 3A:
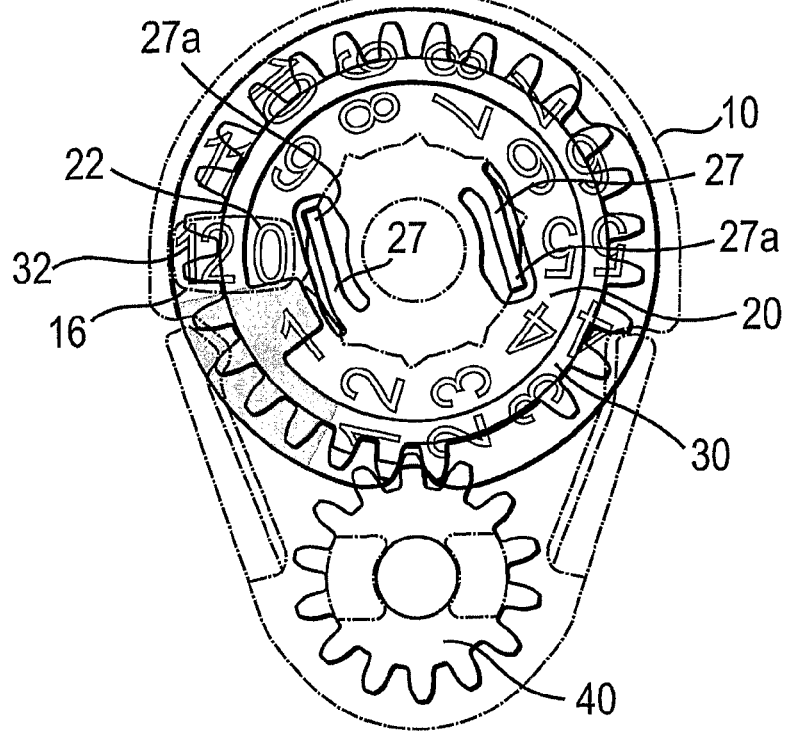
FIGS. 3a and 3b show cut-away views of the dose counter of FIG. 1 at respectively 'count 120' and 'count 119' positions.
Figure 3B:
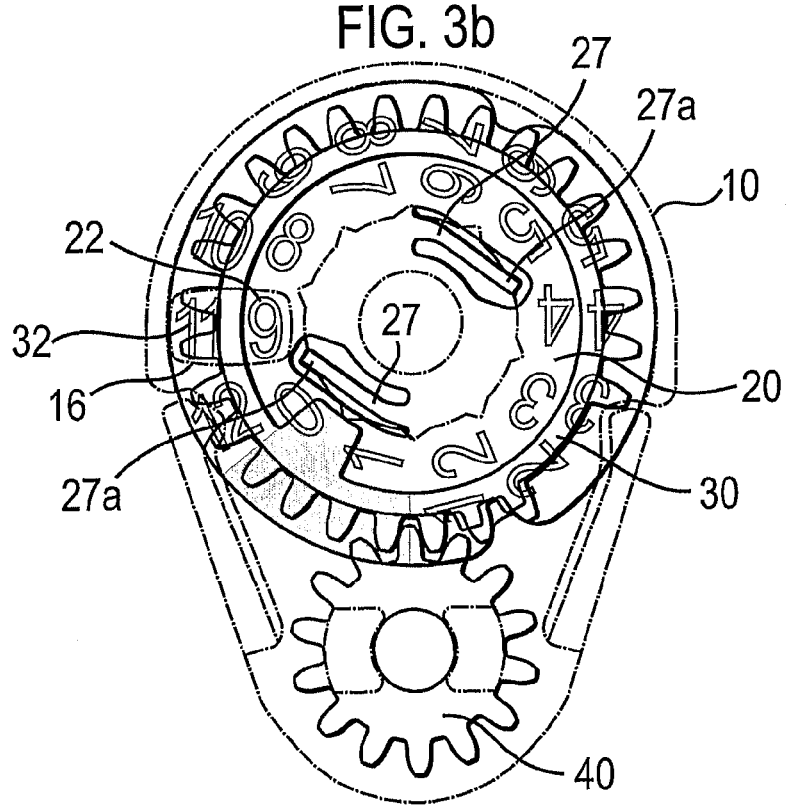
Figure 4A:
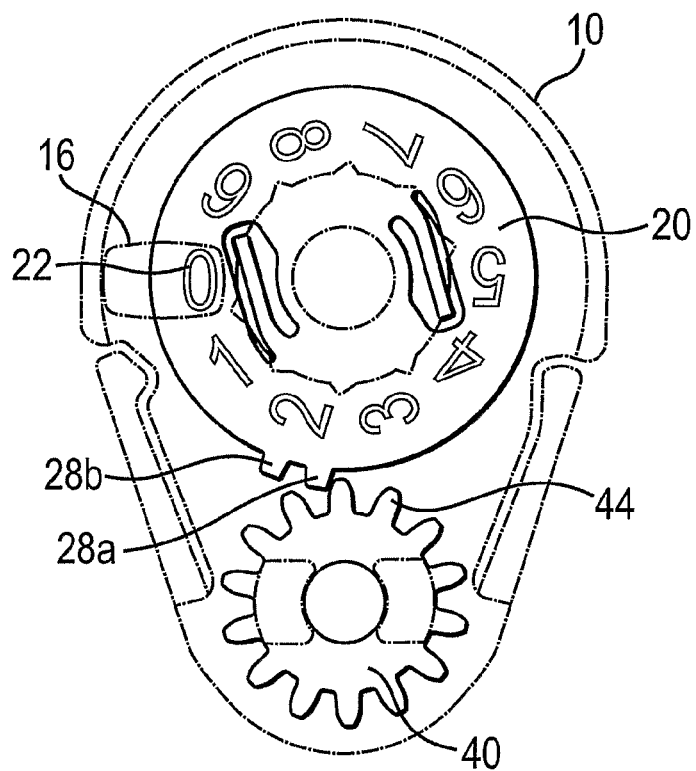
FIGS. 4a and 4b respectively show cut-away views corresponding to FIGS. 3a and 3b of the dose counter of FIG. 1 absent the decimals count wheel.
Figure 4B:
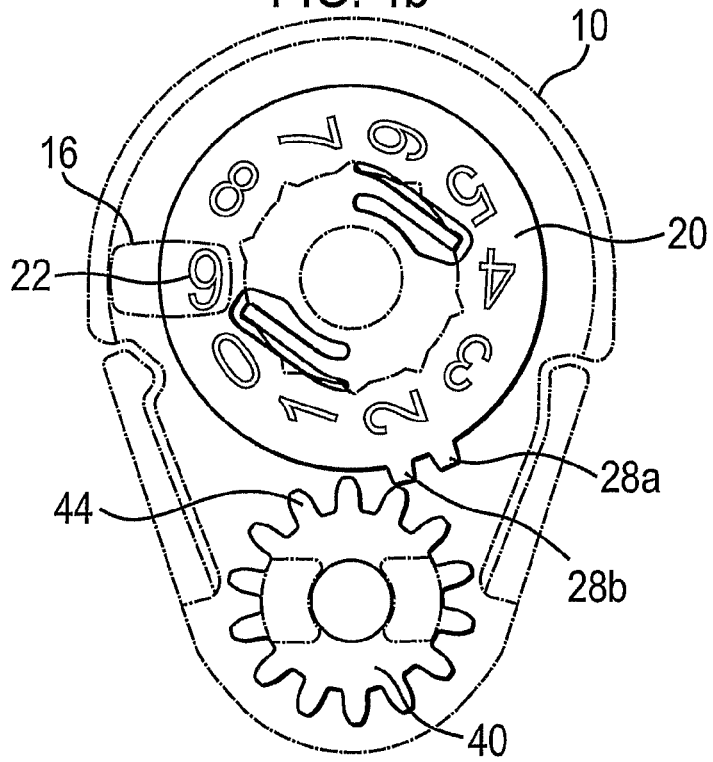
Figure 5A:
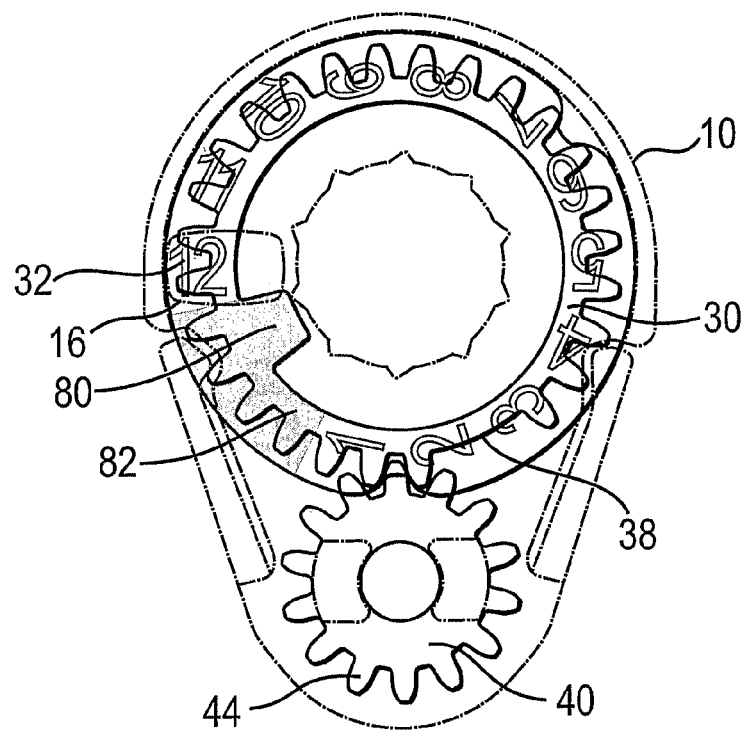
FIGS. 5a and 5b respectively show cut-away views corresponding to FIGS. 3a and 3b of the dose counter of FIG. 1 absent the numerals count wheel.
Figure 5B:
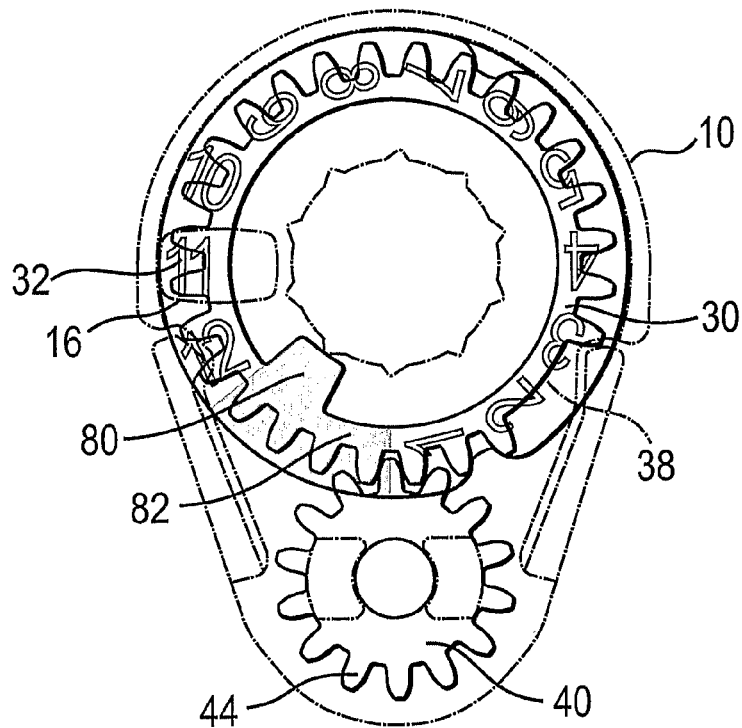

Operation of the dose counter 1 is now described with additional reference to FIGS. 3a to 5b, in which only the most relevant features to the described operation are labelled. The dose counter 1 is arranged to count down and thus, to illustrate a count operation, FIGS. 3a, 4a and 5a show the dose counter 1 at a 'count 120' position and FIGS. 3b, 4b and 5b show the dose counter 1 at a 'count 119' position (i.e. just after counting down from 120).

It will be appreciated that the 'count' of the dose counter 1 referred to in the description of FIGS. 1 to 7 is the count number collectively presented by the count wheels 20, 30 in the window 16.

To initiate a general count operation, ratchet wheel 50 is rotated in response to a driving force being applied to the protrusion 54, which rotation results in rotation of the first count wheel 20 by the interaction of drive tongues 52a, 52b with ratchet drive receipt teeth 24. The ratchet wheel 50 and first count wheel 20 are configured and arranged such that when indexed first count wheel 20 rotates by 36° such that a single indicium 22 thereon is advanced (i.e. the 'units' count moves down one unit).

Where the pre-count operation visible count is x0 (e.g. 120 with 'x=12', as shown at FIGS. 3a, 4a and 5a), the counting action resulting from the use operation is subtly different. Once again, ratchet wheel 50 is rotated to cause rotation of the first count wheel 20 by 36° such that the 'unit' indicium 22 moves on from '0' to '9' (as shown at FIGS. 3b and 4b). This rotation of the first count wheel 20 however, also brings the pair of index teeth 28a, 28b into meshed relationship with the kick teeth 44 of kick wheel 40 such that the kick wheel 40 rotates and in turn, causes the second count wheel 30 to rotate through meshing of their respective teeth 34,44. The wheels 20, 30, 40 are configured and arranged such that the resultant rotation of the second count wheel 30 is by 360/14° (that is to say by 360/n° wherein n is the number of number spacings, where in this case n=14 because there are twelve decimals indicia 32; one shutter portion 80 and one coloured portion 82) such that a single indicium 32 thereon is advanced (i.e. the 'tens' count moves down exactly one unit). In this instance, the decimal indicium 32 moves down from '12' to '11', as shown in FIGS. 3b and 5b.

Where the previous visible count was 10 (i.e. x=1), the counting action resulting from the use operation is again subtly different in that the kick wheel 40 action, as described above, results in the coloured (e.g. red) portion 82 of the second count wheel 30 being advanced into place in the window 16 such that the next display is 'red 9' (i.e. coloured portion 82; and numerals indicia 22 is number 9).

Figure 6A:
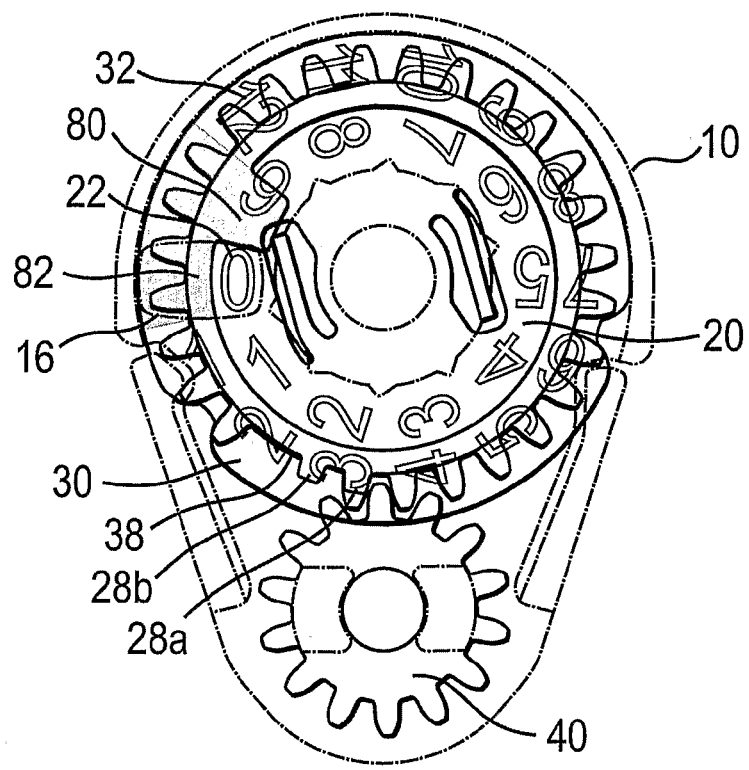
FIGS. 6a and 6b show cut-away views of the dose counter of FIG. 1 at respectively 'count_0' and 'shuttered' positions.
Figure 6B:
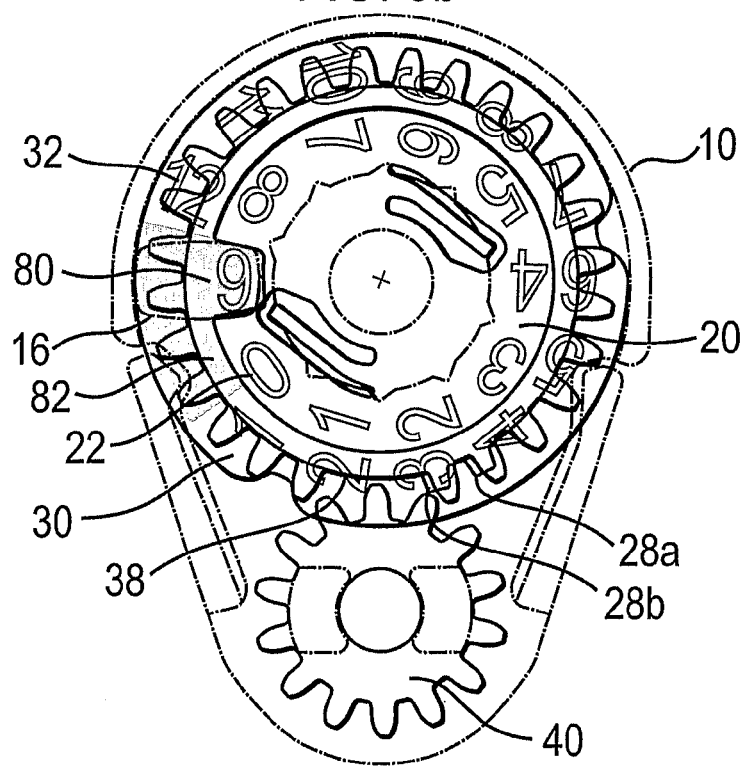
Figure 7A:
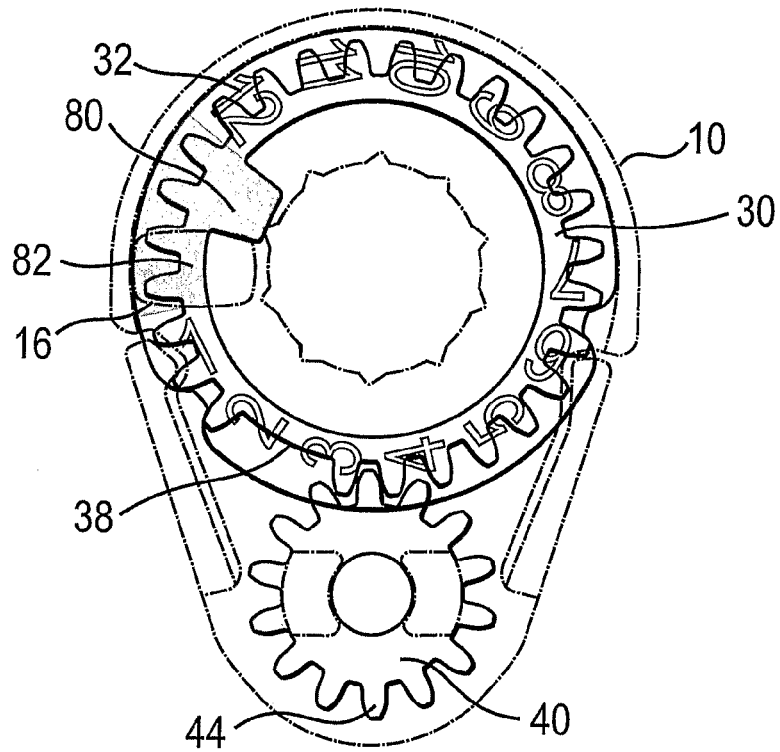
FIGS. 7a and 7b respectively show cut-away views corresponding to FIGS. 6a and 6b of the dose counter of FIG. 1 absent the numerals count wheel.
Figure 7B:
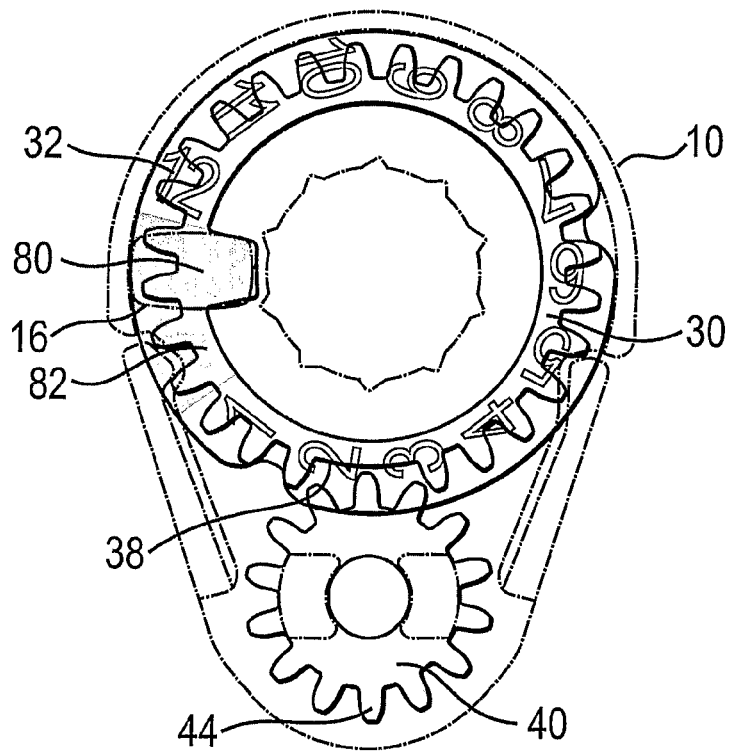

As shown at FIGS. 6a and 7a, where the previous visible count was 'red 0' (i.e. x=0), the counting action resulting from the use operation is still again subtly different in that the kick wheel 40 action, as described above, results in the shutter portion 80 of the second count wheel 30 being advanced into place in the window 16 such that the next display is fully shuttered off (i.e. no indicia 22, 32 visible at all, as shown at FIGS. 6b and 7b). Additionally, the stop position 38 in the set of second count wheel teeth 34 is brought into opposed relation with the kick teeth 44 whereby the kick teeth 44 and the teeth 34 no longer mesh. Thus, if the first count wheel 20 continues to rotate, e.g. in response to continued user operation of a medicament dispenser into which the dose counter 1 is incorporated, notwithstanding that all medicament doses (or all doses in the prescribed regime to which the original counter setting corresponded) have been dispensed, the index teeth 28a, 28b of the first count wheel 20 will still intermittently mesh with the kick teeth 44 to cause the kick wheel 40 to rotate. However, this rotation of the kick wheel 40 will not be transmitted to the second count wheel 30, due to the missing teeth of stop position 38, and the shutter 80 remains in the shuttering position in the window 16 so that the underlying 'units' indicium 22 remains unseen.

To further illustrate the countdown display of the counter 1, the reader's attention is drawn to Table 1 below. Table 1 shows the sequential countdown for each of the units (first) and decimals (second) count wheels 20, 30 upon succeeding use operations or actuations of the counter 1, and also indicates which of these two count wheels 20, 30 indexes to bring the counter 1 to its new counter display. As shown in Table 1, the first (units) count wheel 20 indexes on each counter actuation, whereas the second (decimals) count wheel 30 only indexes (through the kick wheel 40 supra) each time the units indicium 22 of the first (units) count wheel 20 in the window 16 decrements from '0' to '9'. At the end of the countdown, when the display is shuttered, the first count wheel 20 is still free to rotate, underneath the shutter 80 so as not to be visible, and no further indexing of the second count wheel 30 occurs due to the stop position 38 providing for disengagement of the teeth 34, 44 of the second count wheel 30 and the kick wheel 40.

TABLE 1

| Sequential Counter Display in Window | Decimals Wheel Count in Window | Units Wheel Count in Window | Indexing of Units Wheel to this Count? | Indexing of Decimal Wheel to this Count? |
|---|---|---|---|---|
| 120 | 12 | 0 | — | — |
| 119 | 11 | 9 | Yes | Yes |
| 118-110 | 11 | 8 to 0 | Yes | No |
| 109 | 10 | 9 | Yes | Yes |
| 108-100 | 10 | 8 to 0 | Yes | No |
| 99 | 9 | 9 | Yes | Yes |
| 98-90 | 9 | 8 to 0 | Yes | No |
| 89 | 8 | 9 | Yes | Yes |
| 88-80 | 8 | 8 to 0 | Yes | No |
| 79 | 7 | 9 | Yes | Yes |
| 78-70 | 7 | 8 to 0 | Yes | No |
| 69 | 6 | 9 | Yes | Yes |
| 68-60 | 6 | 8 to 0 | Yes | No |
| 59 | 5 | 9 | Yes | Yes |
| 58-50 | 5 | 8 to 0 | Yes | No |
| 49 | 4 | 9 | Yes | Yes |
| 48-40 | 4 | 8 to 0 | Yes | No |
| 39 | 3 | 9 | Yes | Yes |
| 38-30 | 3 | 8 to 0 | Yes | No |
| 29 | 2 | 9 | Yes | Yes |
| 28-20 | 2 | 8 to 0 | Yes | No |
| 19 | 1 | 9 | Yes | Yes |
| 18-10 | 1 | 8 to 0 | Yes | No |
| 9 | 'Red' | 9 | Yes | Yes |
| 8-0 | 'Red' | 8 to 0 | Yes | No |
| Shuttered | Shuttered | Shuttered | Yes | Yes |

The ratchet wheel 50 is adapted to not only rotate in the cavity 23 of the first count wheel 20 in a first sense (clockwise as viewed in FIG. 1), but also to rotate in an opposite, second sense (i.e. anti-clockwise) in the first count wheel cavity 23. However, while rotation of the ratchet wheel 50 in the first sense drivably rotates the first count wheel 20 in the first sense for indexing of the units count 22 in the window 16, rotation of the ratchet wheel 50 in the opposite, second sense is relative to the first count wheel 20; i.e. the first count wheel 20 remains stationary so that the units indicia 22 in the window 16 remains unchanged. That is to say, frictional engagement between the respective wheels 20, 50 does not result in reverse rotation of the first count wheel 20, except for tolerance adjustments as discussed below.

To this end, the first count wheel 20 is provided with a pair of diametrically opposed resilient tongues or pawls 27 which co-operate with a serrated circumferential surface 11 of a circular cavity 13 from which the first spindle 12 projects. The serrated surface 11 comprises plural shaped indentations 15 with which the free ends 27a of the pawls 27 engage.

As the skilled person will understand, and as evident by comparison of FIG. 3a with FIG. 3b, for example, as the first count wheel 20 is driven by the ratchet wheel 50 to rotate in the first sense, the free ends 27a of the pawls 27 move out of engagement with the indentation 15 presently engaged with and into engagement the next adjacent indentation 15 in the first sense. This then indexes the first count wheel in its new position, at which the next units indicia 22 in the count sequence registers with the window 16. However, the engagement of the free ends 27a of the pawls in the indentations 15 prevents the first count wheel 20 rotating back in the opposite, second sense as the ratchet wheel 50 so rotates.

As will also be appreciated by the skilled person, the shaping of the indentations 15 is such as to provide tolerances in the indexing rotation of the first count wheel 20 by the ratchet wheel 50. In other words, the first count wheel 20 can be slightly over-rotated in the first sense, but as the ratchet wheel 50 rotates back in the opposite, second sense it carries the first count wheel 20 in the same sense, through frictional forces, until the pawls 27 engage the "overshot" indentations 15 which then prevent further reverse rotation of the first count wheel 20 and indexes the units indicia 22 in the window 16.

The reverse rotation of the ratchet wheel 50 in the opposite, second sense resets the ratchet wheel 50 for the next counting event. This reverse rotation, like the forward rotation, is achievable through co-operation of the protrusion 54 with a complementary feature in the medicament dispenser (not shown) which moves, e.g. reciprocates, upon actuation of the medicament dispenser.

As shown in FIG. 2a, for example, the housing 10 is also provided at its periphery with a pair of resilient tongues or pawls 17. The housing pawls 17 are adapted to aid accurate alignment of the decimals indicia 32 in the window 16. To this end, the housing pawls 17 each have a free end 17a which engages between the teeth 34 of the second count wheel 30 to maintain the second count wheel 30 in each of the rotary orientations at which it is set, firstly in manufacture and then, in use, by the kick wheel 40. In more detail, and as will be understood by the skilled person in the art, as the second count wheel 30 is incrementally rotated by the kick wheel 40, the housing pawls 17 are deflected outwardly to enable the second count wheel teeth 34 to pass by. The housing pawls 17, however, inhibit or prevent reverse rotation of the second count wheel 30.

Having now described the housing pawls 17, an explanation can now be given for the pair of indentations 39 provided in the top face 37 of the second (decimals) count wheel 30. The indentations 39 are assembly features which enable the second count wheel 30 to be easily mounted into the housing 10, about the first spindle 12, notwithstanding the presence of the housing paws 17. Specifically, when assembling the counter 1, the second count wheel 30 is oriented with the indentations 39 in registration with the free ends 17a of the housing pawls 17. The second count wheel 30 can then be inserted into the housing 10 with the free ends 17a passing through the indentations 39.

Figure 8:
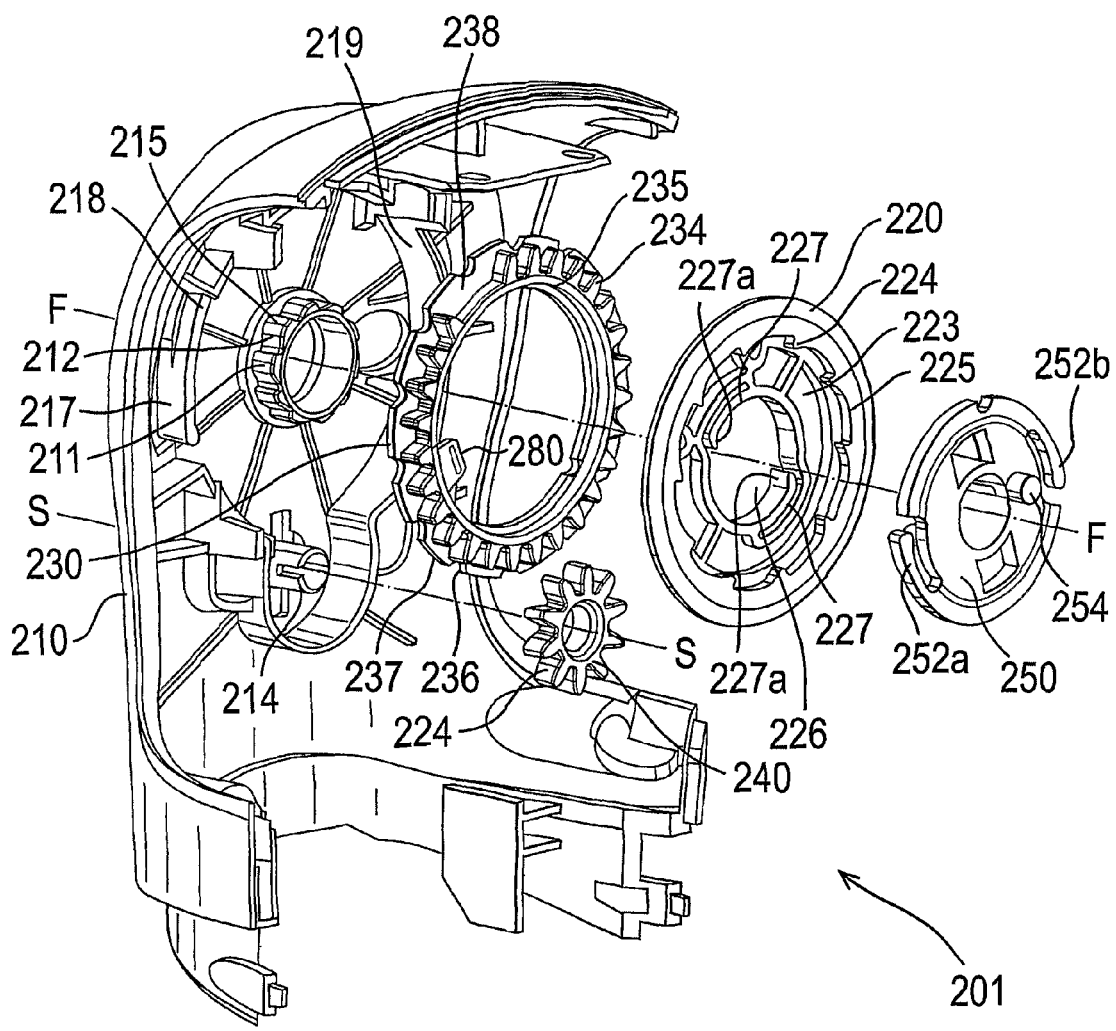
FIG. 8 shows an exploded view of a second dose counter in accordance with the present invention.

Referring now to FIG. 8, this shows a second counter 201 in accordance with the present invention. For the avoidance of duplication, those features of the second counter 201 which correspond to those of the first counter 1 are indicated by like reference numerals and will not be described in detail, except where necessary.

The countdown operation of the second counter 201 is identical to the first counter 1, and as shown in Table 1 supra. That is to say, each actuation of the counter 201 causes the ratchet wheel 250 to index the first (units) count wheel 220 and, when the counter actuation causes the number 222 displayed by the first count wheel 220 in the window 216 to change from '0' to '9'; the first and second count wheels 220, 230 are simultaneously indexed as a result of the fixed index teeth 228a, 228b of the first count wheel 220 engaging the kick wheel teeth 244 to cause the kick wheel 240 to turn and its teeth 244 to turn the second count wheel 230 through the meshing engagement with the second count Wheel teeth 234. At the end of the countdown sequence, the stop position 238 in the second count wheel teeth 234 registers with the kick wheel teeth 244 so that, while the first count wheel 220 can continue to rotate, underneath the shutter 280, upon continued actuation driving the ratchet wheel 250, further intermittent rotation of the kick wheel 240 caused by the fixed index teeth 228a, 228b is unable to be transmitted to the second count wheel 230 so that the shutter 280 remains in place in the window 216.

In this embodiment, the housing 210 is a part of a housing for a medicament dispenser (not shown). As may be best seen from FIG. 10a, the first 220 and second 230 count wheels are in concentric relationship, but the level of the second count wheel 230 is slightly raised relative to that of the first count wheel 220 to enable shutter 280 to protrude over and above the first count wheel 220.

In a subtle aspect, it may be seen that the profile of all teeth 234, 244 has a flanged form, which is selected to optimise the various toothed engagements necessary for effective gearing and inter-operability of the parts of the counter.

In the second counter 201, reverse rotation of the first count wheel 220 is prevented through the inter-engagement of the free ends 227a of the resilient pawls 227 with ratchet teeth 215 provided on the outer peripheral surface 211 of the first spindle 212.

Figure 10A:
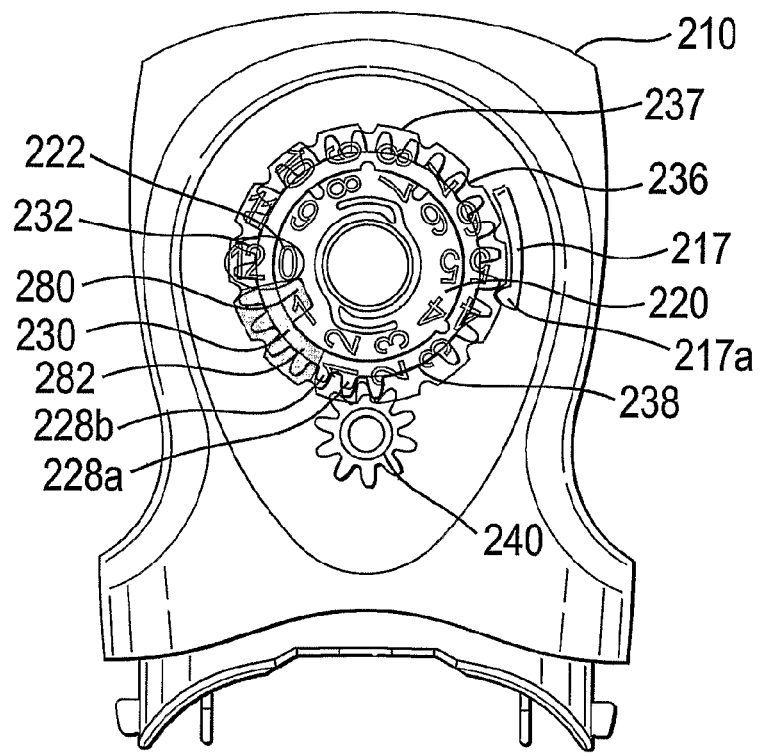
FIGS. 10a and 10b show cut-away views of the second dose counter at respectively 'count 120' and 'count 119' positions.
Figure 10B:
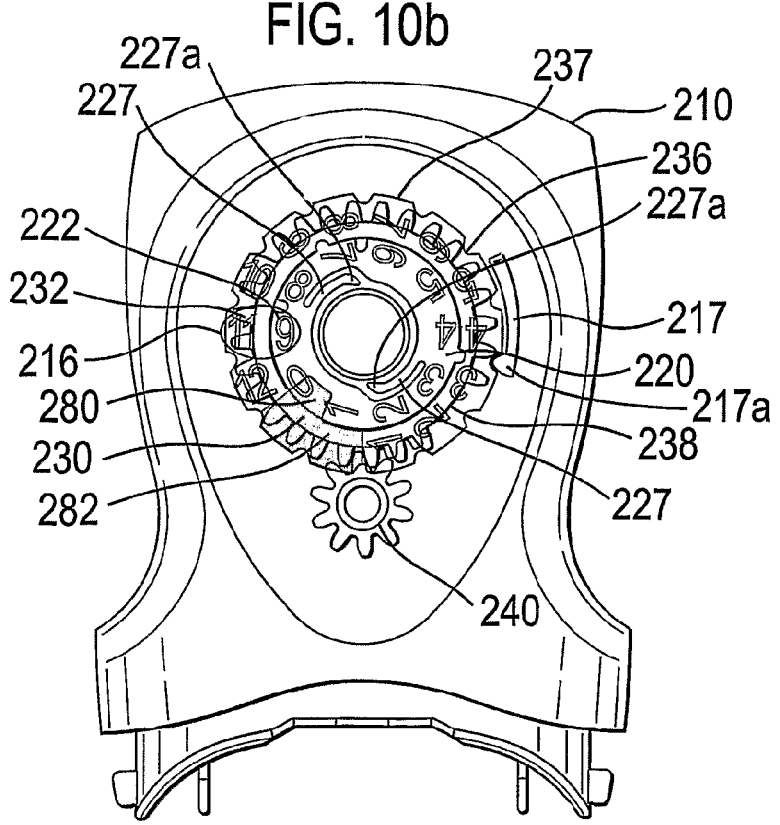
Figure 11A:
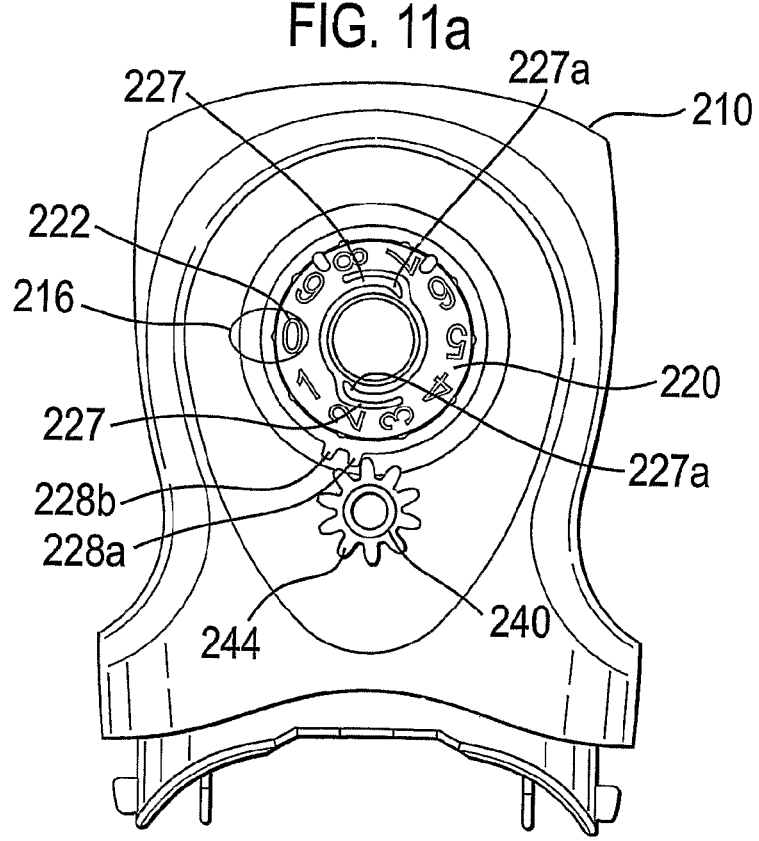
FIGS. 11a and 11b respectively show cut-away views corresponding to FIGS. 10a and 10b absent the decimals count wheel.
Figure 11B:
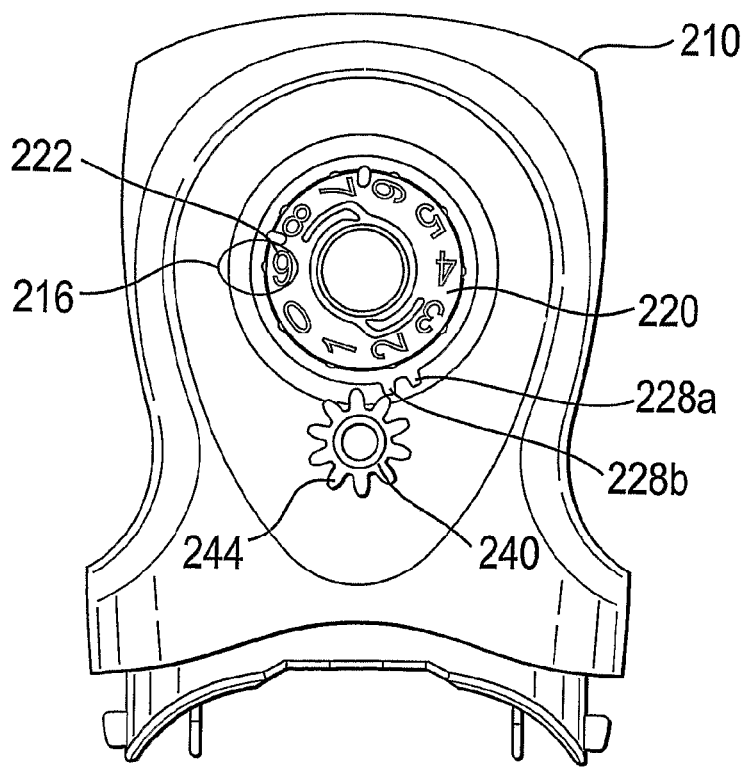
Figure 12A:
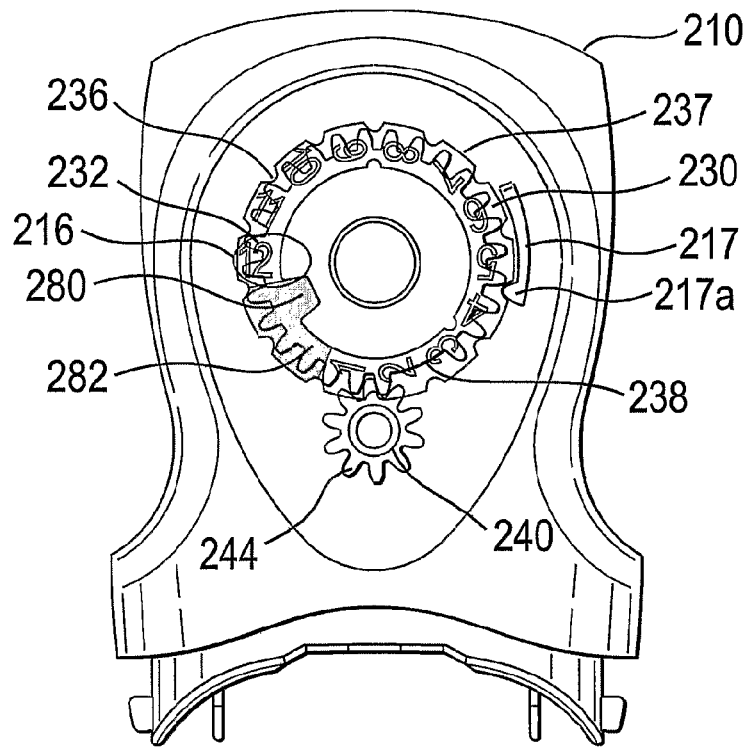
FIGS. 12a and 12b respectively show cut-away views corresponding to FIGS. 10a and 10b absent the numerals count wheel.
Figure 12B:
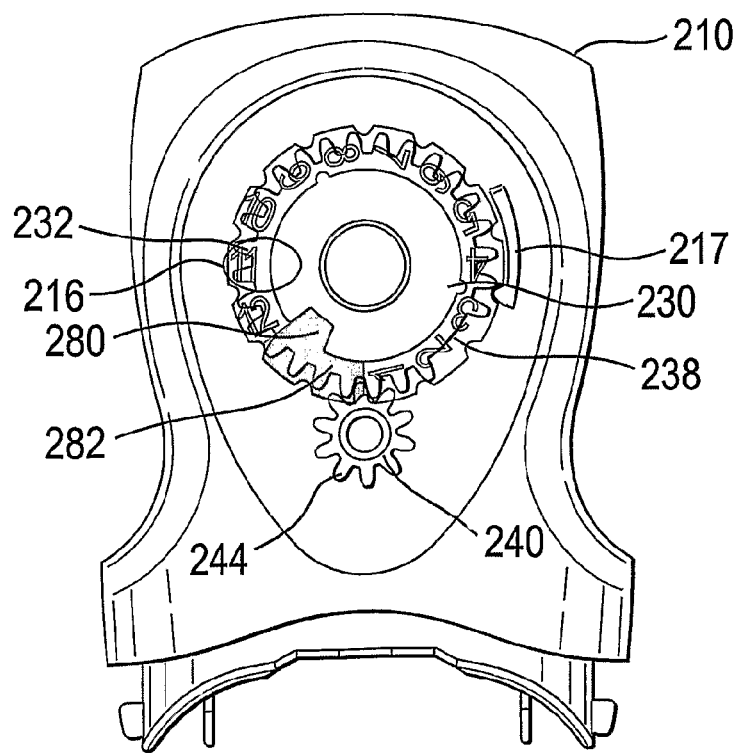
Figure 13A:
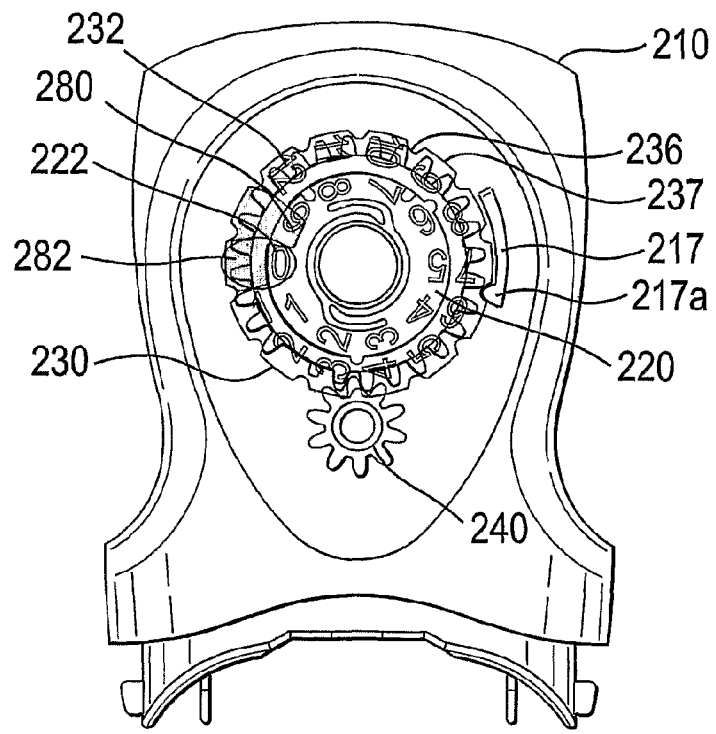
FIGS. 13a and 13b show cut-away views of the second dose counter at respectively 'count_' and 'shuttered' positions.
Figure 13B:
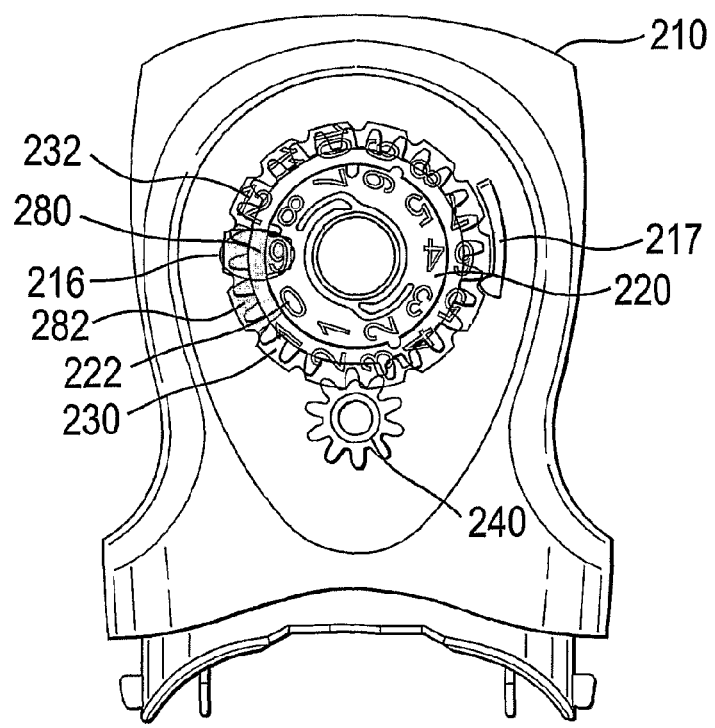
Figure 14A:
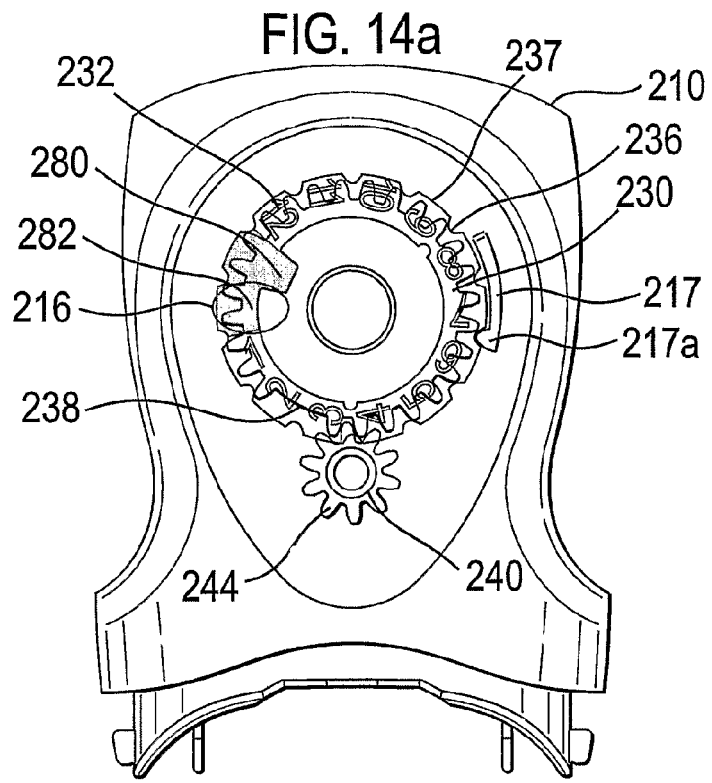
FIGS. 14a and 14b respectively show cut-away views corresponding to FIGS. 13a and 13b absent the numerals count wheel.
Figure 14B:
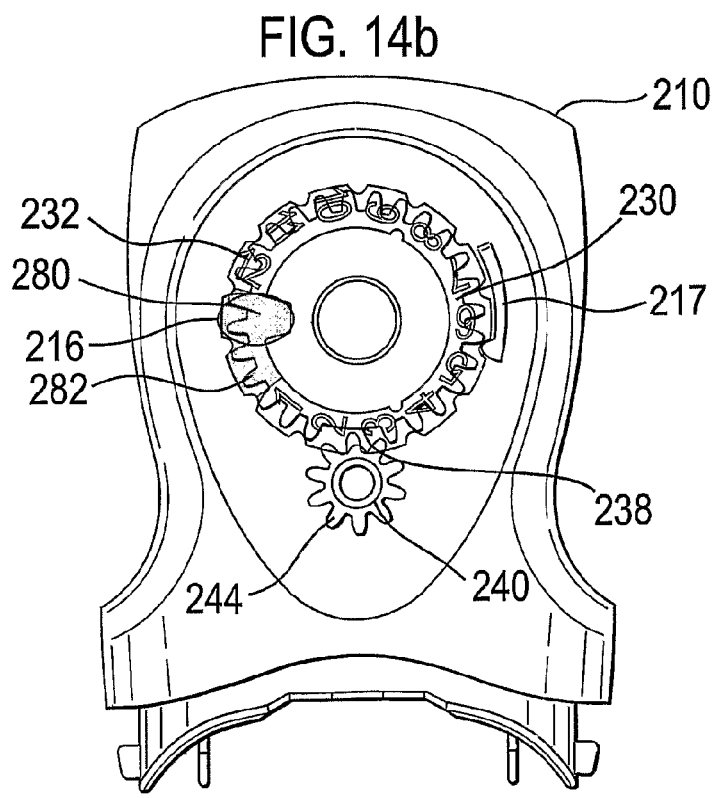

The housing 210 of the second counter 201 further provides a resilient pawl 217. In this embodiment there is only a single pawl 217 and the free end 217a of the pawl 217 engages in indentations 236 in the outer circumferential surface of the top face 237 of the second count wheel 230, as shown in FIGS. 10a and 10b, for instance. There is one indentation 236 for each count or index position of the second count wheel 230, so the free end 217a of the pawl 217 and the indentations 236 provide an indexing function which provides for accurate alignment of the decimals indicia 234 in the window 216.

The indentations 236 in this embodiment have a symmetrical shape, more particularly a generally U-shape. However, other shapes could be used. Moreover, asymmetric shapes could also be used, For instance, it may be useful for the flanks of the indentations 236 to present different angles, for example for the trailing (rear) flanks of the indentations 236 (relative to the direction of rotation of the second count wheel 230, e.g. anti-clockwise in FIGS. 10a and 10b) to form a greater angle with a central radial line through the indentations 236 than the leading (forward) flanks. This means there is less resistance to the pawl 217 releasing from the indentations 236 as the second count wheel 230 is driven by the kick wheel 240.

It will be appreciated that the above usage of the counters 1; 201 has been described in terms of a counter arranged to count downwards (i.e. to count on from 'n+1' to 'n' on indexing), but that the counter may be modified to count upwards (i.e. instead to count on from 'n' to 'n+1' on indexing).

In these embodiments of the invention, the second count wheel 30; 230 is integrally formed with the shutter portion 80; 280.

The components of the counter and any assemblies and sub-assemblies described above may be made from any suitable materials such as plastic polymer materials (e.g. acetal or ABS or styrene polymers).

In a modification of the first and second counters 1; 201 (not shown), the friction resistance between the kick wheel 40; 240 and its spindle mounting 14; 214 may be increased to provide a dragging or braking effect which retards the speed of rotation of the kick wheel 40; 240 when driven by the first count wheel 20; 220. One possible way to achieve this is through the provision of axially-oriented splines about the outer periphery of the spindle mounting 14; 214. This may prevent or inhibit any tendency for the second count wheel 30; 230 to be misaligned or over-indexed by a fast moving kick wheel 40; 240.

The dose counter is for use with a medicament dispenser for delivering a plurality of doses (ordinarily of uniform/unit dosage amount) of a medicament formulation, such as metered dose inhaler (MDI) type devices in which, generally actuation is responsive to an actuating movement (e.g. push down the MDI canister) relative to its housing; reservoir dry powder inhalers (RDPI); multi-dose dry powder inhalers (MDPI) in which an elongate form blister strip is advanced to enable release of medicament from the individual blisters thereof; other types of multi-dose dry powder inhalers (MDPI) in which, generally dose advancement to a delivery position is responsive to a dose advancement movement (e.g. rotating a circular blister pack to move the next blistered dose to the delivery position) relative to a housing; and reservoir liquid spray inhalers (RLSI) in which, generally metering is responsive to a metering movement (e.g. bring metering cavity into communication with the bulk reservoir) relative to the bulk reservoir.

The dose counter may be for use with the MDI type devices disclosed in any of the US provisional patent applications previously incorporated herein by reference.

It will be understood that the present disclosure is for the purpose of illustration only and the invention extends to modifications, variations and improvements thereto.

The invention claimed is:

1. A dose counter for use with a medicament dispenser, said dose counter comprising
 a ratchet;
 a first count wheel arranged to rotate about a first axis of rotation, said first count wheel including one or more ratchet drive receipt elements arranged thereon for receipt of drive from said ratchet to rotate the first count wheel about said first axis of rotation;
 a second count wheel arranged to rotate about the first axis of rotation, said second count wheel including a set of teeth arranged annularly thereon; and
 a kick wheel arranged to rotate about a second axis of rotation offset from the first axis of rotation, said kick wheel including a set of kick teeth arranged annularly thereon and in meshed relationship with the set of teeth of the second count wheel such that rotary motion of the kick wheel results in rotary motion of the second count wheel,
 wherein said first count wheel further includes at least one fixed index tooth arranged for intermittent meshing with the kick teeth of the kick wheel such that rotary motion of the kick wheel results from rotary motion of the first count wheel only when said intermittent meshing occurs.

2. The dose counter of claim 1 configured and arranged so that said intermittent meshing is able to occur a plurality of times.

3. The dose counter of claim 1, wherein the ratchet is a ratchet wheel arranged for rotation about the first axis of rotation.

4. The dose counter of claim 3, wherein the first count wheel is provided with a circular cavity that is arranged for receipt of the ratchet, and the ratchet drive receipt elements are arranged about the inner circumferential wall of the cavity for ratcheted drive interaction with the ratchet.

5. The dose counter of claim 1, wherein the ratchet is provided with one or more ratchet drive tongues.

6. The dose counter of claim 1, wherein said one or more ratchet drive receipt elements are arranged annularly about the first count wheel.

7. The dose counter of claim 1, wherein the one or more ratchet drive receipt elements are selected from the group consisting of one or more teeth and indents.

8. The dose counter of claim 1, wherein at least one of the first and second count wheels has the form of a disc or a ring.

9. The dose counter of claim 8, wherein the first count wheel has the form of a ring that is arranged for disposed receipt of the ratchet, and the ratchet drive receipt elements are arranged about the inner circumferential wall of the ring for ratcheted drive interaction with the ratchet.

10. The dose counter of claim 1, wherein the ratchet is provided with at least one drive receipt element for receipt of drive that results in movement thereof.

11. The dose counter of claim 10, wherein said at least one drive receipt element comprises at least one protrusion.

12. The dose counter of claim 10, wherein the at least one drive receipt element is offset to the first axis.

13. The dose counter of claim 1, wherein the second count wheel teeth are arranged circumferentially on the second count wheel.

14. The dose counter of claim 1, wherein the second count wheel is arranged concentric to the first count wheel.

15. The dose counter of claim 1, wherein the second count wheel takes the form of a ring and the first count wheel is disposed within the ring.

16. The dose counter of claim 1, wherein the set of teeth of the second count wheel are provided on an outwardly-facing circumferential surface thereof.

17. The dose counter of claim 1, wherein the kick teeth are arranged circumferentially on the kick wheel.

18. The dose counter of claim 1, wherein the at least one index tooth is fixed at a point at or about the circumference of the first count wheel and rotation of the first count wheel is arranged to bring the at least one index tooth into meshed relationship with the kick teeth of the kick wheel at a particular point of the rotary cycle of the first count wheel such that meshing of each index tooth occurs once during each complete rotation of the first count wheel.

19. The dose counter of claim 1, having a reverse rotation mechanism for interacting with either one or both count wheels to prevent reverse movement thereof.

20. The dose counter of claim 1 additionally comprising a housing.

21. The dose counter of claim 20, wherein said housing is shaped to define the first axis of rotation and the second axis of rotation.

22. The dose counter of claim 21, wherein the first count wheel and/or the second count wheel mounts to the housing for rotation about the first axis of rotation and the kick wheel mounts to the housing for rotation about the second axis of rotation.

23. The dose counter of claim 20, wherein the housing takes the form of a bezel.

24. The dose counter of claim 1, wherein the first and second count wheels are adapted in use to rotate about the first axis in the same sense.

25. The dose counter of claim 1, which includes a viewing window through which the count may be viewed.

26. The dose counter of claim 25 having a shutter to close off the viewing window at a predetermined point in the dose counter operation.

27. The dose counter of claim 26, wherein the shutter is comprised in one of the count wheels.

28. The dose counter of claim 27, wherein the count wheel is integrally formed with the shutter.

29. The dose counter of claim 27, wherein the shutter overlies the other count wheel.

30. The dose counter of claim 27, wherein the shutter is comprised in the second count wheel.

31. The dose counter of claim 1 having a display region through which the first and second count wheels are rotatable and a shutter which is movable to a shuttering position in which it shutters the display region.

32. The dose counter of claim 31 which is so configured and arranged that the shutter is only movable to the shuttering position when the first and second count wheels are in predetermined angular positions about the first axis.

33. The dose counter of claim 31 configured and arranged so that the shutter is only able to be moved to the shuttering position when the first count wheel has rotated through a plurality of revolutions about the first axis.

34. The dose counter of claim 31 configured and arranged such that the shutter moves to its shuttering position in response to movement of at least one of the count wheels.

35. The dose counter of claim 34, wherein the at least one count wheel is the second count wheel.

36. The dose counter of claim 34, wherein the at least one count wheel and the shutter have cooperating parts through which, in use, the at least one count wheel moves the shutter to its shuttering position.

37. The dose counter of claim 31, wherein the shutter is moved to its shuttering position by the at least one count wheel.

38. The dose counter of claim 37, wherein the shutter is carried to the shuttering position by the at least one count wheel.

39. The dose counter of claim 31 configured and arranged to display a count sequence with the count wheels and to cause the shutter to move to its shuttering position at the end of the count sequence.

40. The dose counter of claim 1 having count indicia on the count wheels.

41. The dose counter of claim 40, wherein the count indicia are arranged on the first and second count wheels so as to be on concentric paths.

42. The dose counter of claim 1 configured and arranged to sequence from a count mode of operation, in which the first count wheel is able to drive rotation of the second count wheel through the kick wheel, to a non-count mode of operation, in which the first count wheel is unable to drive rotation of the second count wheel through the kick wheel.

43. The dose counter of claim 42 configured and arranged to sequence from the count mode to the non-count mode when the first count wheel has completed a predetermined number of revolutions about the first axis.

44. The dose counter of claim 42 which is adapted to sequence from the count mode to the non-count mode when the second count wheel is disposed in a predetermined angular orientation about the first axis.

45. The dose counter of claim 42 configured and arranged such that in the non-count mode meshing of the kick teeth with the at least one index tooth and/or the second count wheel teeth is unable to occur.

46. The dose counter of claim 45, wherein a gap is provided in the set of kick teeth or the second count wheel teeth to disable meshing in the non-count mode.

47. The dose counter of claim 1, wherein the ratchet is movable in a first, driving direction to drivably rotate the first count wheel in a first sense through engagement of the ratchet with the ratchet drive receipt elements of the first count wheel and in a second, non-driving direction relative to the first count wheel.

48. The dose counter of claim 47, wherein the ratchet is a ratchet wheel mounted for rotation about the first axis of rotation and the first, driving direction is rotation of the ratchet wheel in the first sense and the second, non-driving direction is rotation of the ratchet wheel in the second, opposite sense.

49. A dose counter for counting the number of doses of medicament dispensed from a medicament dispenser comprising:
    first and second count wheels which are concentrically arranged for rotation on a common axis of rotation, each count wheel having count indicia thereon;
    a display region positioned for the count indicia of each count wheel to register with and display the count of the counter;
    a ratchet for incrementally rotating the first count wheel in a predetermined sense to change the count indicia thereof registering with the display region; and
    a mechanism adapted to intermittently transmit the incremental rotation of the first count wheel into an incremental rotation of the second count wheel in a predetermined sense to change the count indicia thereof registering with the display region.

50. The dose counter of claim 49, wherein the mechanism is adapted to only intermittently transmit the rotation of the first count wheel to the second count wheel at the same predetermined point in each cycle of rotation of the first count wheel.

51. The dose counter of claim 49, wherein the predetermined senses are in the same sense.

52. The dose counter of claim 49, wherein the count indicia on the count wheels are such as to provide a countdown count in the display region.

53. The dose counter of claim 49, wherein the mechanism is a gear mechanism.

54. The dose counter of claim 49, wherein the count indicia are arranged on the first and second count wheels so as to be on concentric paths.

55. The dose counter of claim 49, wherein the ratchet is movable in a first, driving direction to drive incremental rotation of the first count wheel in the predetermined sense and in a second, non-driving direction relative to the first count wheel.

56. The dose counter of claim 55, wherein the ratchet is a ratchet wheel mounted for rotation about the common axis of rotation and the first, driving direction is rotation of the ratchet wheel in the predetermined sense and the second, non-driving direction is rotation of the ratchet wheel in an opposite sense.

* * * * *